United States Patent [19]

Tovey et al.

[11] Patent Number: 5,470,316
[45] Date of Patent: Nov. 28, 1995

[54] BODY TISSUE PENETRATING DEVICE HAVING A VACUUM INDICATOR

[75] Inventors: H. Jonathan Tovey, Milford, Conn.; Sidney D. Autry, Bellingham, Wash.

[73] Assignee: United States Surgical Corporation, Norwalk, Conn.

[21] Appl. No.: 206,686

[22] Filed: Mar. 4, 1994

Related U.S. Application Data

[63] Continuation of Ser. No. 116,789, Sep. 7, 1993, abandoned.

[51] Int. Cl.$^6$ .................................................. A61M 1/00
[52] U.S. Cl. ............................................ 604/118; 604/168
[58] Field of Search ........................... 604/117, 118, 604/158, 168

[56] References Cited

U.S. PATENT DOCUMENTS

| | | | |
|---|---|---|---|
| 2,623,521 | 12/1952 | Shaw . | |
| 3,763,860 | 10/1973 | Clarke . | |
| 3,980,082 | 9/1976 | Miller | 604/118 |
| 4,162,673 | 7/1979 | Patel . | |
| 4,175,567 | 11/1979 | Patel . | |
| 4,186,750 | 2/1980 | Patel . | |
| 4,215,699 | 8/1980 | Patel . | |
| 4,254,762 | 3/1981 | Yoon . | |
| 4,299,230 | 11/1981 | Kubota . | |
| 4,356,826 | 11/1982 | Kubota . | |
| 4,535,773 | 8/1985 | Yoon . | |
| 4,613,325 | 9/1986 | Abrams | 604/118 |
| 4,623,335 | 11/1986 | Jackson | 604/118 |
| 4,645,491 | 2/1987 | Evans | 604/158 |
| 4,808,168 | 2/1989 | Warring . | |
| 4,940,458 | 7/1990 | Cohn . | |
| 4,944,724 | 7/1990 | Goldberg et al. | 604/118 |
| 4,973,312 | 11/1990 | Andrew | 604/158 |
| 4,994,035 | 2/1991 | Mokros | 604/118 |
| 5,066,288 | 11/1991 | Deniega et al. . | |
| 5,139,485 | 8/1992 | Smith et al. . | |
| 5,209,721 | 5/1993 | Wilk . | |
| 5,217,441 | 6/1993 | Shichman . | |
| 5,256,148 | 10/1993 | Smith et al. | 604/158 |
| 5,258,003 | 11/1993 | Ciaglia et al. . | |
| 5,352,206 | 10/1994 | Cushieri et al. | 604/164 |

FOREIGN PATENT DOCUMENTS

| | | |
|---|---|---|
| 0484725 | 5/1992 | European Pat. Off. . |
| 0520296 | 12/1992 | European Pat. Off. . |
| 1616107 | 4/1971 | Germany . |
| 537677 | 1/1977 | U.S.S.R. . |

OTHER PUBLICATIONS

Derwin English Language Abstract of German Publication No. DT 2919–390 (Nov. 1980).

*Primary Examiner*—Paul J. Hirsch

[57] ABSTRACT

The present invention relates to an apparatus and method for penetrating body tissue. The apparatus includes a handle member having a gas pressure chamber positioned therein and a shaft member having a longitudinal bore therethrough and one end connected to the handle member. The longitudinal bore in the shaft member is in cooperative alignment with the gas pressure chamber to facilitate the passage of gases therethrough. The apparatus also includes a pressure indicating system which provides a visual indication when the shaft member has penetrated the body tissue.

18 Claims, 2 Drawing Sheets

BODY TISSUE PENETRATING DEVICE HAVING A VACUUM INDICATOR

This is a continuation of application U.S. Ser. No. 08/116,789 filed Sep. 7, 1993, now abandoned.

BACKGROUND OF THE INVENTION

1. Field of the Invention

The present invention relates to an apparatus for penetrating body tissue. More particularly, the present invention relates to a pneumoperitoneum needle and/or a trocar having a vacuum system which connects to a vacuum source to provide an indication when the needle or trocar penetrates the body tissue.

2. Description of the Related Art

Pneumoperitoneum needles have been used to insufflate the abdominal cavity to facilitate laparoscopic and endoscopic examination and surgery of body tissue. One type of pneumoperitoneum needle, commonly known as the Veress-type pneumoneedle, includes a spring loaded blunt stylet in a larger diameter hollow needle. Once the pneumoneedle penetrates the abdominal wall and enters a body cavity, the resistance against the end of the needle ceases and the spring pushes the blunt end of the stylet forward so that it extends beyond the sharp tip of the needle. Thus when the needle penetrates the body tissue the sharp tip of the needle is prevented from puncturing or lacerating intraabdominal structures.

Another Veress-type pneumoneedle is described in U.S. Pat. No. 5,139,485 to Smith et al. That needle has a sharpened outer needle which allows passage of a blunt inner needle within the outer needle. In addition, the needle contains a position indicator within the outer needle which indicates whether the needle is in a protective or non-protective position. An acoustical enhancement mechanism is described which amplifies the sound of the inner needle moving to the protective position.

In contrast to these type needles, the present invention provides a new and cost effective apparatus and method for detecting penetration of the peritoneum or other body portions by a hollow needle or like instrument.

SUMMARY OF THE INVENTION

The present invention provides an apparatus for penetrating body tissue. The apparatus includes a handle member having a gas pressure chamber positioned therein and a shaft member having one, end connected to a distal end of the handle member. Preferably, the shaft member has a longitudinal bore which is in cooperative alignment with at least a portion of the gas pressure chamber so as to allow the passage of gases therethrough. A pressure indicating system responsive to the passage of gases through the shaft member is positioned within the gas pressure chamber and provides a visual indication when a free end of the hollow shaft member has penetrated the body tissue.

Generally, the pressure indicating system includes a piston positioned within the gas pressure chamber which is movable between a normal position and an indicating position, biasing means for moving the piston to the normal position and indicating means for providing a surgeon with a visual indication when the piston moves to the indicating position. Preferably, the gas pressure chamber includes a viewing window which permits observation of at least a portion of the gas pressure chamber so the surgeon can observe the indicating means. In one embodiment, the indicating means includes an indicating arm with one end secured to the piston and a free end which can be viewed from the viewing window when the piston is in the indicating position. In an alternative embodiment, the indicating means includes a bar line which is positioned on the piston and can be viewed from the viewing window.

The apparatus of the present invention also includes a connector port which is secured to the handle member. The connector port has a bore therethrough which provides a passageway between the gas pressure chamber and an outer surface portion of the handle member. A valve system may be secured to the connector point to allow selective regulation of the ingress or egress of gases through the gas pressure chamber.

In an alternative embodiment, the apparatus of the present invention includes a housing having a pressure chamber positioned therein which is adapted for hand gripping, and means extending from the housing for penetrating body tissue. Preferably, the penetrating means is a hollow needle which has a passageway. The passageway is in aligned communication with at least a portion of the pressure chamber to facilitate the passage of gases therethrough. The apparatus also includes means positioned within the pressure chamber for indicating when a free end portion of the penetrating means has penetrated the body tissue. Generally, the indicating means is at least partially responsive to the passage of gas through the passageway.

The present invention also relates to a method for penetrating body tissue which includes the step of providing an apparatus for penetrating body tissue. Preferably, the apparatus has a handle member with a gas pressure chamber positioned therein and a shaft member having one end connected to a distal end of the handle member. The shaft member has a longitudinal bore therethrough which is in cooperative alignment with at least a portion of the gas pressure chamber so as to facilitate the passage of gases therethrough. The apparatus also includes a pressure indicating system which is positioned within the gas pressure chamber and is responsive to the passage of gases therethrough. The indicating system indicates when a free end of the hollow shaft member has penetrated the body tissue.

The method of the present invention also includes the steps of connecting a vacuum source to the handle member, positioning a distal end of the shaft member against the body tissue, and applying pressure to the handle member so that the shaft member penetrates the body tissue and the pressure indicating system indicates penetration of the body tissue.

BRIEF DESCRIPTION OF THE DRAWINGS

The preferred embodiments of the invention are described hereinbelow with reference to the drawings wherein.

DETAILED DESCRIPTION OF THE PREFERRED EMBODIMENTS

Figure 1:
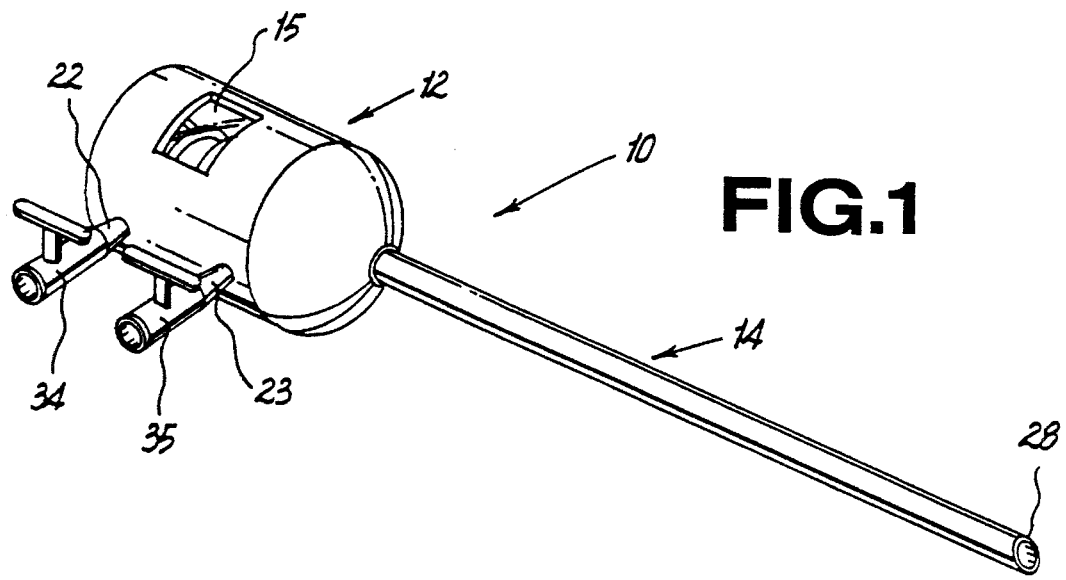
FIG. 1 is a perspective view of an exemplary needle assembly configured in accordance with the present invention and illustrating a vacuum chamber having a bar indicator therein.
Figure 2:
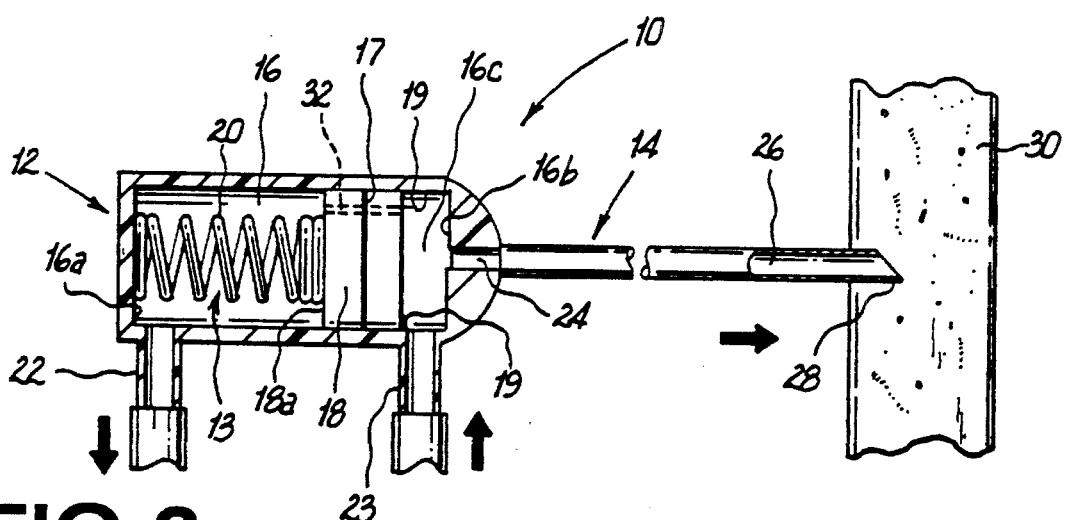
FIG. 2 is a side view in partial cross-section of the needle assembly of FIG. 1 without the stopcocks, illustrating the needle tip inserted into the body tissue and the piston in a normal position.

The apparatus of the present invention is provided to penetrate body tissue, e.g., the abdominal wall, and to provide an indication to the physician that the body tissue has been penetrated. As shown in FIGS. 1 and 2, one embodiment of the apparatus of the present invention is a pneumoperitoneum needle 10 having a handle 12 and a hollow needle shaft 14. Preferably, handle 12 is cylindrical in shape and includes pressure indicating system 13.

Referring to FIG. 2, pressure indicating system 13 includes gas pressure chamber 16, piston 18 and spring 20. Pressure chamber 16 is formed within handle 12 and is configured and dimensioned to receive piston 18. Piston 18 is slidably positioned within chamber 16 and is movable between a normal position and an indicating position. Spring 20 is secured within chamber 16 between the proximal side 18a of piston 18 and the proximal end portion 16a of chamber 16, as shown in FIG. 2. In this configuration, spring 20 biases piston 18 toward the distal end 16b of chamber 16 until distal side 18b of the piston engages flange 19, i.e., the piston is moved to the normal position, when gases are prevented from flowing through channel 26 and chamber 16, as shown. Flange 19 is provided to maintain a space 16c between piston 18 and distal end 16b to allow insufflation gas to flow from connection port 23 to aperture 24. One skilled in the art would know to select a spring with appropriate tension forces to bias the piston toward the distal end of the chamber when no gas is flowing through the needle shaft and one which compresses when a particular gas pressure flows through the needle shaft.

Figure 3:
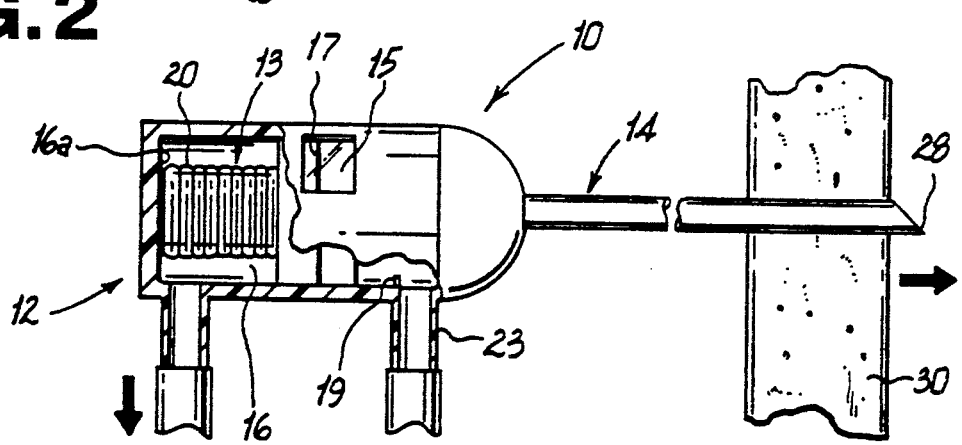
FIG. 3 is a side view in partial cross-section similar to FIG. 2, illustrating the needle tip which has penetrated the body tissue and the piston in an indicating position.

The indicating position of piston 18 is shown in FIG. 3. Generally, the indicating position is the position of piston 18 within chamber 16 in which a marking on piston 18, such as bar line 17, is visible through window 15 of handle 12. Preferably, window 15 is fabricated from a clear rigid material, such as plexiglass.

Connection port 22 is secured to handle 12 at a point proximal to piston 18 and is provided to connect apparatus 10 to an external gas pressure source. Stopcock 34 may be connected to connection port 22 to regulate the flow of gases through the connection port. Insufflation connection port 23 is secured to handle 12 at a point distal to piston 18 and is provided to facilitate insufflation or desufflation of body cavities once pneumoperitoneum needle 10 is inserted therein. Stopcock 35 is connected to connection port 23 to regulate the flow of insufflation gas through connection port 23. Typically, when penetrating the body cavity, stopcock 35 is closed so as to maintain the gas pressure within chamber 16. On the other hand, when insufflating the body cavity, stopcock 34 is closed so as to maintain the gas pressure within chamber 16.

Needle shaft 14 includes channel 26 extending longitudinally through needle shaft 14 and is secured to the distal end of handle 12 so that aperture 24 of handle 12 is in aligned communication with channel 26. In this configuration, air or other gases may pass between channel 26, gas pressure chamber 16 and connection port 22 and actuate pressure indicating system 13. Preferably, the distal end 28 of needle shaft 14 is beveled to facilitate penetration of the body tissue 30.

Figure 4:
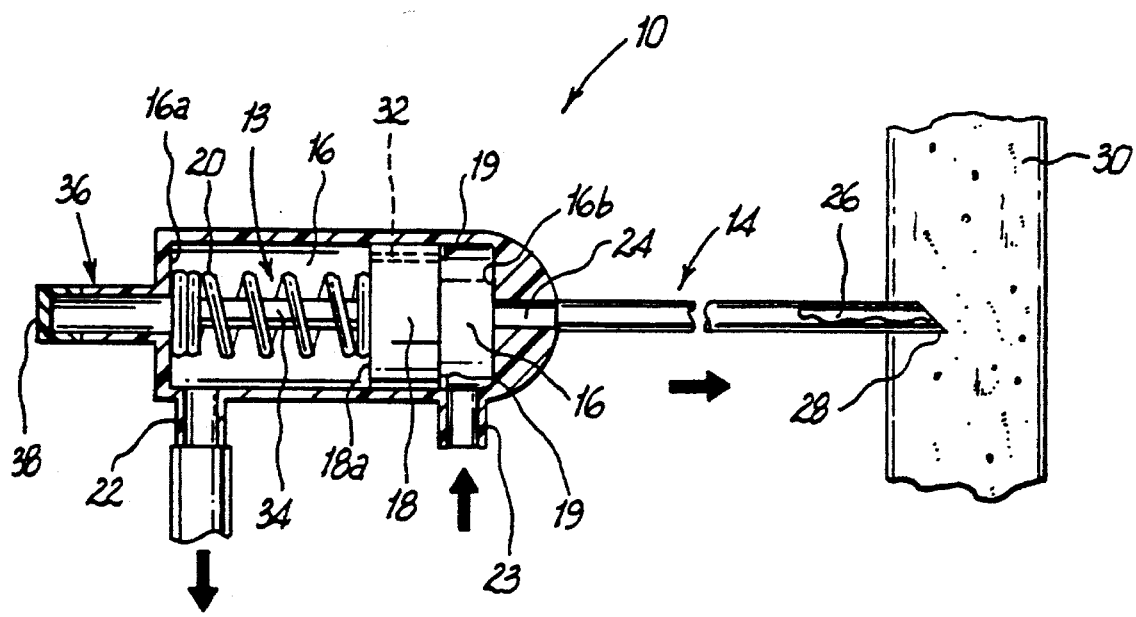
FIG. 4 is a side view in partial cross-section similar to FIG. 2, illustrating an alternative embodiment for the indicating feature of the present invention.
Figure 5:
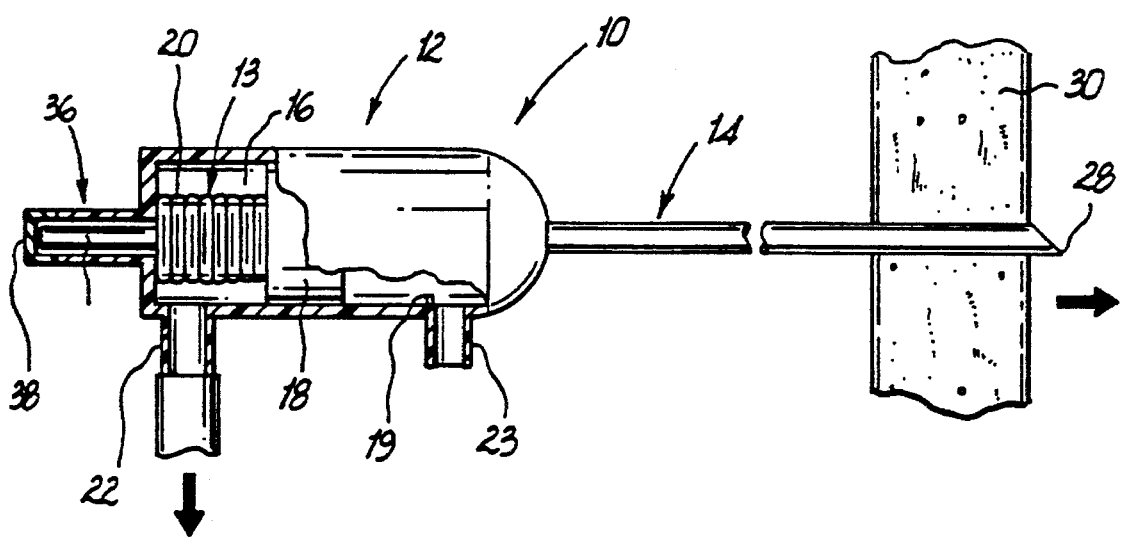
FIG. 5 is a side view in partial cross-section similar to FIG. 3, illustrating an indicating arm visible through the alternative indicating window.

Referring to FIGS. 4 and 5 an alternative embodiment for the indicating feature of the present invention is shown. In this embodiment, one end of indicating arm 34 is connected to proximal side 18a of piston 18 and extends outwardly therefrom. The free end of arm 34 reciprocates within window portion 36 of handle 12 in response to movement of piston 18 between the normal position and the indicating position. Preferably, window 38 of window portion 36 is fabricated from a clear rigid material such as plexiglass.

When piston 18 is in the normal position the free end of indicating arm 34 is not visible through window 38, as shown in FIG. 4. However, when piston 18 is in the indicating portion the free end of indicating arm 34 is visible through window 38, as shown in FIG. 5, thus providing the surgeon with an indication that needle shaft 14 has penetrated the body tissue.

In operation, a vacuum source (not shown) is connected to connection port 22 via a suitable hose, causing air or other gases to flow through channel 26 of needle shaft 14 to create a differential pressure across piston 18. The differential pressure across the piston 18 causes the piston to move to the indicating position, thus compressing spring 20. Airflow is indicated by bar line 17 which is visible through window 15, as shown in FIG. 3.

When the needle engages the body tissue, shown in FIG. 2, the airflow through channel 26 is inhibited. The differential pressure across piston 18 is equalized through bleed hole 32 in piston 18. Equalization of the pressure across piston 18 causes the piston to move distally under the action of spring 20 to the normal position. As noted, in the normal position bar line 17 is no longer visible through window 15, thus providing an indication that there is no airflow through channel 26 and that needle shaft 14 has not penetrated the body tissue.

Once distal end 28 of needle shaft 14 penetrates the body tissue and enters a body cavity as shown in FIG. 3, the airflow through channel 26 is restored, thus causing piston 18 to move to the indicating position so that bar line 17 is visible to the surgeon through window 15, thus indicating penetration of the body tissue.

After penetrating the body tissue, the body cavity is insufflated. As noted above, to insufflate the body cavity stopcock 34 is closed and stopcock 35 is opened to allow the insufflation gas to enter the cavity via aperture 24 and connector port 23.

It will be understood that various modifications can be made to the embodiments of the present invention herein disclosed without departing from the spirit and scope thereof. For example, various sizes of the instrument are contemplated, as well as various types of construction materials. Also, various modifications may be made in the configuration of the parts. Therefore, the above description should not be construed as limiting the invention but merely as exemplifications of preferred embodiments thereof. Those skilled in the art will envision other modifications within the scope and spirit of the present invention as defined by the claims appended hereto.

What is claimed is:

1. Apparatus for penetrating body tissue, which comprises:

a shaft member having a pressure chamber positioned at a proximal end thereof and a free distal end adapted to penetrate body tissue, said pressure chamber being in gaseous communication with said free distal end; and a pressure change indicator slidably mounted within the pressure chamber for sensing and indicating a pressure change adjacent said free distal end.

2. The apparatus according to claim 1, further comprising a window visually accessing said pressure chamber, said window being associated with said pressure change indicator to permit observation thereof.

3. The apparatus according to claim 2, wherein said pressure change indicator comprises:
   a piston slidably positioned within said pressure chamber and movable between a first position and a second position; and
   a biasing spring engageable with said piston to maintain said piston in said first position.

4. The apparatus according to claim 3, wherein said pressure change indicator further comprises an indicating arm having one end secured to said piston and a free end which can be observed from said window.

5. The apparatus according to claim 3, wherein said pressure change indicator further comprises a marking positioned on said piston which can be observed from said window.

6. Apparatus for penetrating body tissue, which comprises:
   a handle member having a gas pressure chamber positioned therein;
   a shaft member having a longitudinal bore therethrough and a first end connected to a distal end of said handle member and extending outwardly therefrom to a second free end, said free end having tissue penetrating means thereon, said longitudinal bore being in communication with said gas pressure chamber to facilitate the passage of gas therein; and
   a pressure change indicator slidably mounted within said gas pressure chamber and operatively associated with said longitudinal bore for sensing and indicating a pressure change adjacent the second free end.

7. The apparatus according to claim 6, wherein said gas pressure chamber includes a viewing window which permits observation of at least a portion of said gas pressure chamber.

8. The apparatus according to claim 7, wherein said pressure change indicator comprises:
   a piston slidably positioned within said gas pressure chamber, said piston being movable between a first position and a second position; and
   a biasing spring engageable with said piston to maintain said piston in said first position.

9. The apparatus according to claim 8, wherein said pressure change indicator further comprises an indicating arm having one end secured to said piston and a free end which can be viewed from said viewing window when said piston is in said indicating position.

10. The apparatus according to claim 8, wherein said pressure change indicator further comprises a marking, positioned on said piston which can be viewed from said viewing window.

11. The apparatus according to claim 8, wherein said piston includes a bleed hole to facilitate equalization of gas pressure across said piston.

12. The apparatus according to claim 8, wherein said piston moves to said first position when gas is prevented from passing through said gas pressure chamber.

13. The apparatus according to claim 8, wherein said piston moves to said second position when gas passes through said gas pressure chamber.

14. The apparatus according to claim 6, further comprising a connector port connected to said handle member, said connector port having a bore therethrough which provides a passageway between said gas pressure chamber and an outer surface portion of said handle member.

15. The apparatus according to claim 14, wherein said connector port includes valve means to selectively regulate the flow of gases through said gas pressure chamber.

16. Apparatus for penetrating body tissue, which comprises:
   a housing adapted for hand gripping and having a pressure chamber positioned therein;
   means extending from said housing to a free end for penetrating body tissue, said penetrating means having a passageway therethrough which is in communication with at least a portion of said pressure chamber; and
   means slidably mounted within said pressure chamber and operatively associated with said passageway for sensing and indicating a pressure change adjacent said free end of said penetrating means.

17. The apparatus according to claim 16, wherein said pressure chamber includes a viewing window which permits observation of at least a portion of said pressure chamber.

18. A method for penetrating body tissue comprising:
   providing an apparatus for penetrating body tissue, said apparatus having a handle member having a gas pressure chamber positioned therein, a shaft member having a longitudinal bore therethrough and one end connected to a distal end of said handle member and extending outwardly therefrom, said longitudinal bore being in cooperative alignment with at least a portion of said gas pressure chamber so as to facilitate the passage of gases therethrough, and pressure change indicating means slidably mounted within said gas pressure chamber for indicating when a free end of said hollow shaft member has penetrated the body tissue in response to a pressure change adjacent said free end of said shaft member;
   connecting a gas pressure source to said handle member; and
   penetrating the body tissue with said apparatus such that after penetration, said pressure change indicating means is activated.

* * * * *